(12) United States Patent
Qiu et al.

(10) Patent No.: US 12,193,987 B2
(45) Date of Patent: Jan. 14, 2025

(54) SYSTEM, APPARATUS, AND METHOD FOR CONTROLLING DEVICES BASED ON SOUND

(71) Applicant: HYTTO PTE. LTD., Singapore (SG)

(72) Inventors: Jilin Qiu, Guangzhou (CN); Dan Liu, Guangzhou (CN)

(*) Notice: Subject to any disclaimer, the term of this patent is extended or adjusted under 35 U.S.C. 154(b) by 0 days.

(21) Appl. No.: 17/671,783

(22) Filed: Feb. 15, 2022

(65) Prior Publication Data

US 2022/0370284 A1    Nov. 24, 2022

Related U.S. Application Data

(63) Continuation-in-part of application No. 16/835,808, filed on Mar. 31, 2020, now Pat. No. 11,452,669, and a continuation-in-part of application No. 16/352,876, filed on Mar. 14, 2019, now Pat. No. 11,311,453.

(51) Int. Cl.
  *A61H 19/00*    (2006.01)
  *A61H 23/02*    (2006.01)

(52) U.S. Cl.
  CPC ......... *A61H 19/30* (2013.01); *A61H 23/0254* (2013.01); *A61H 2201/0153* (2013.01); *A61H 2201/0207* (2013.01); *A61H 2201/1215* (2013.01); *A61H 2201/5005* (2013.01); *A61H 2201/5048* (2013.01); *A61H 2201/5097* (2013.01)

(58) Field of Classification Search
  CPC .............. A61H 19/00–50; A61H 23/00; A61H 23/0254; A61H 2201/0153; A61H 2201/0207; A61H 2201/1215; A61H 2201/5005; A61H 2201/5048; A61H 2201/5097; A61H 2201/5058
  See application file for complete search history.

(56) References Cited

U.S. PATENT DOCUMENTS 3,361,130 A    1/1968  Rowe
5,807,287 A *  9/1998  Cheng ................ A61H 23/0263
                                                              5/915

(Continued)

FOREIGN PATENT DOCUMENTS

KR        101256565 B1 *  4/2019
WO        2006040750 A1   4/2006
WO        2008067487 A2   6/2008

*Primary Examiner* — Tu A Vo
*Assistant Examiner* — Kelsey E Baller

(57) ABSTRACT

The system has an accessory control module, comprising computer-executable code stored in non-volatile memory, a processor, a device of a human user, and an accessory configured to communicate with the device, the accessory including a motor or a heater. The accessory control module, the processor, the device, and the accessory are configured to receive or obtain audio data using the device, identify at least one parameter of the audio data, the at least one parameter having one or more parameter values, convert the one or more parameter values into one or more action signals, and control the motor or the heater using the one or more action signals to perform a predefined act of the accessory at a parameter-dependent intensity synchronously with receiving or obtaining the audio data. The predefined act sexually stimulates the human user.

22 Claims, 12 Drawing Sheets

(56) References Cited

U.S. PATENT DOCUMENTS

| | | | |
|---|---|---|---|
| 6,277,085 B1* | 8/2001 | Flynn | A61H 23/0218 |
| | | | 601/78 |
| 6,368,268 B1 | 4/2002 | Sandvick et al. | |
| 8,255,299 B2 | 8/2012 | Cambridge | |
| 8,644,967 B2* | 2/2014 | Seiler | A43B 3/50 |
| | | | 381/301 |
| 8,936,544 B2 | 1/2015 | Shahoian et al. | |
| 9,762,515 B1 | 9/2017 | Olivares et al. | |
| 10,051,328 B2 | 8/2018 | Olivares, II et al. | |
| 10,218,795 B1 | 2/2019 | Messinger | |
| 10,483,784 B2* | 11/2019 | Konik | A61H 19/34 |
| 10,576,013 B1 | 3/2020 | Sloan | |
| 11,134,041 B1 | 9/2021 | He | |
| 2002/0065477 A1* | 5/2002 | Boyd | A61H 19/44 |
| | | | 601/DIG. 16 |
| 2002/0133103 A1 | 9/2002 | Williams et al. | |
| 2003/0036678 A1 | 2/2003 | Abbassi | |
| 2004/0082831 A1* | 4/2004 | Kobashikawa | A61H 19/32 |
| | | | 600/38 |
| 2004/0097852 A1* | 5/2004 | Boyd | A61H 19/40 |
| | | | 601/48 |
| 2005/0138560 A1 | 6/2005 | Lee et al. | |
| 2006/0247561 A1* | 11/2006 | Chiu | A61H 23/0236 |
| | | | 601/46 |
| 2007/0055096 A1* | 3/2007 | Berry | A61H 19/32 |
| | | | 600/38 |
| 2012/0179077 A1* | 7/2012 | Tuck | A61H 19/44 |
| | | | 601/46 |
| 2012/0259171 A1 | 10/2012 | Shmakov | |
| 2012/0304216 A1 | 11/2012 | Strong | |
| 2013/0165747 A1 | 6/2013 | Maggs | |
| 2014/0011557 A1 | 1/2014 | Coyle | |
| 2014/0115690 A1 | 4/2014 | Huang et al. | |
| 2015/0186853 A1* | 7/2015 | Suzukake | G06Q 20/06 |
| | | | 705/41 |
| 2015/0328082 A1* | 11/2015 | Jiang | A61H 23/02 |
| | | | 600/38 |
| 2016/0049043 A1 | 2/2016 | Tennenhaus et al. | |
| 2017/0119619 A1 | 5/2017 | Dills | |
| 2018/0116904 A1 | 5/2018 | Lieberman et al. | |
| 2019/0133877 A1 | 5/2019 | Cambridge | |
| 2020/0009009 A1* | 1/2020 | Nishida | A63F 13/215 |
| 2020/0276504 A1 | 9/2020 | Liu | |
| 2020/0289363 A1 | 9/2020 | Liu | |
| 2020/0315908 A1* | 10/2020 | Liu | A61H 19/30 |
| 2020/0357046 A1* | 11/2020 | McGann | A61H 23/006 |
| 2020/0366972 A1 | 11/2020 | Sloan | |
| 2021/0341992 A1 | 11/2021 | Cambridge | |
| 2022/0141550 A1 | 5/2022 | Liu | |

* cited by examiner

IOS device implementation for local music

```
// Create music player class
let player = try AVAudioPlayer(contentsOf: url)
var value = 0
player.updateMeters()
var sum: Float = 0.0

// Traverse and calculate the intensity information of all music channels
for index in 0..<player.numberOfChannels {
    sum = sum + pow(10, player.averagePower(forChannel: index) / X)
}

// take the average
var normalizedValue = sum/Float(player.numberOfChannels)
if normalizedValue > 1 {
    normalizedValue = 1
}
normalizedValue = normalizedValue * 2 * X // Limit upper and lower limits
value = normalizedValue * 101
if value > 101 { value = 101 }
if value < 0 { value = 0 }

// send the intensity value command to the toy
toyManager.sendOrder(value)
```

*Fig. 5*

```
IOS device implementation for online music
// Get music analysis data through API
MusicDownLoadManager.shared.start(urlString: "https//api.spotify.com/v1/audio-
analysis/\(self.models[index].id)", id: self.models[index].id, success: { [weak self] (id, analysisModel) in
    var frequencyModels = [MusicFrequencyViewModel]()

// Traverse and calculate all music stream fragments
    for se in segments {
        if let duration = se.duration, let loudness_start = se.loudness_start, let loudness_max =
se.loudness_max {
            let duration = Int(duration * Float(100))
            var m: int = 0
            XX
        }
    }
}

// Play music synchronously
    self.sptPlayer?.playSpotifyURI(url, startingWith: 0, startingWithPosition: 0, callback: { [weak self] (error) in
        // The music progress and the segment intensity of the music stream are synchronized every X
seconds.
        self.timer = Timer.scheduledTimer(withTimeInterval: x, block: { [weak self] (timer) in
            guard let duration = self.sptPlayer?.metadata.currentTrack?.duration, let position =
self.sptPlayer?.playbackState?.position else {
                return
            }
            self.sptTempProgress = position
            let po_index = lroundf(Float(po)) * 100
            // send the intensity value command to the toy
            self.setToyOrder(at: frequencyModels[po_index])
        }, repeats: true)
        RunLoop.main.add(self.timer!, forMode: RunLoop.Mode.common)
    })
}, failure: nil)
```

*Fig. 6*

```
IOS device implementation for listening to external sounds

// Set the microphone's receiving sound information
let setting = [
                AVSampleRateKey:44100.0 as AnyObject,
                AVNumberOfChannelsKey:2 as AnyObject,
                AVEncoderAudioQualityKey:0 as AnyObject
              ]

// Create microphone handling class
self.recorder = try AVAudioRecorder(url: URL(fileURLWithPath: "\(folder)/xxx"), settings: setting)
self.recorder?.isMeteringEnabled = true
self.recorder?.prepareToRecord()
self.recorder?.record()

// Get the characteristics of the captured sound
recorder.updateMeters()

// Calculate sound information
let averagePower = recorder.averagePower(forChannel: 0)
var normalizedValue = pow(10, averagePower/x)*5
if normalizedValue > 1 {
     normalizedValue = 1
}
normalizedValue = normalizedValue * self.rate * x
var value = normalizedValue * 2 * y
if value > y { value = y }
if value < 0 { value = 0 }

// Send instructions to the toy
let orders = self.orderConvertValue(at: Int(value), toyPlayModel: toyPlayModel)

// send the intensity value command to the toy
self.sendOrders(at: orders, toy: toy)
```

*Fig. 7*

```
Android device implementation for local music
MediaPlayer mPlayer = new MediaPlayer(); // Create media player
mPlayer.setDataSource(mAudioPath); // Set the path of the audio file to be played
mPlayer.prepare();
mPlayer.start();
int sessionId = mPlayer.getAudioSessionId(); // get sessionId
Visualizer visualizer = new Visualizer(sessionId); // get visualization tools through sessionId
equalizer = new Equalizer(0, sessionId);
equalizer.setEnabled(true);
visualizer.setCaptureSize(Visualizer.getCaptureSizeRange()[1]);
visualizer.setDataCaptureListener(new Visualizer.OnDataCaptureListener() {
    /**
     * Convert music fft spectrum data to toy intensity
         * @param visualizer
         * @param fft,  FFT data sampling and take the average
          * @param samplingRate
    */
      @Override
      public void onFftDataCapture(Visualizer visualizer, byte[] fft, int samplingRate) {
        double[] divideAverage = divideAverage(fft);
                double maxAve = 0;
                for (int i = 0; i < divide; i++) {
                        shift(fftAverage[i], divideAverage[i]);
                        double tempD = divideAverage[i] * 1.0 / average(fftAverage[i]);
                        maxAve = Math.max(maxAve, tempD);
                }
                int order = 0;

......
                }
        if (listener != null && mIsPlaying)
                    listener.callback(true, order);// Intensity event callback }, Visualizer.getMaxCaptureRate() / 2, false, true);
visualizer.setScalingMode(Visualizer.SCALING_MODE_NORMALIZED);
visualizer.setEnabled(true);
```

*Fig. 8*

Android device implementation for online music

```
SpotifyPlayer.Builder builder = new SpotifyPlayer.Builder(config); // Get spotify player
AudioTrackInstantiation mAudioTrackInstantiation = new AudioTrackInstantiation(); // Customize the
implementation of the AudioController interface
builder.setAudioController(mAudioTrackInstantiati); // Set interface callback int sessionId = mAudioTrackInstantiation.getAudioSessionId(); // get sessionId
Visualizer visualizer = new Visualizer(sessionId); // get visualization tools through sessionId
equalizer = new Equalizer(0, sessionId);
equalizer.setEnabled(true);
visualizer.setCaptureSize(Visualizer.getCaptureSizeRange()[1]);
visualizer.setDataCaptureListener(new Visualizer.OnDataCaptureListener() {
    /**
     * Convert music fft spectrum data to toy intensity
         * @param visualizer
         * @param fft, FFT data sampling and take the average
          * @param samplingRate
     */
     @Override
     public void onFftDataCapture(Visualizer visualizer, byte[] fft, int samplingRate) {
        double[] divideAverage = divideAverage(fft);
                double maxAve = 0;
                for (int i = 0; i < divide; i++) {
                        shift(fftAverage[i], divideAverage[i]);
                        double tempD = divideAverage[i] * 1.0 / average(fftAverage[i]);
                        maxAve = Math.max(maxAve, tempD);
                }
...
                }
        if (listener != null && mIsPlaying)
                    listener.callback(true, order);// Intensity event callback }, Visualizer.getMaxCaptureRate() / 2, false, true);
visualizer.setScalingMode(Visualizer.SCALING_MODE_NORMALIZED);
visualizer.setEnabled(true);
```

*Fig. 9*

```
Android device implementation for listening to external sounds
        // get MediaRecorder
File soundFile = new File(output_path);
        MediaRecorder recorder = new MediaRecorder();
        recorder.setAudioSource(MediaRecorder.AudioSource.MIC);// The sound source is the microphone
        recorder.setOutputFormat(MediaRecorder.OutputFormat.AMR_NB);// Set format
        recorder.setAudioEncoder(MediaRecorder.AudioEncoder.DEFAULT);// Set the decoding method
        recorder.setOutputFile(soundFile.getAbsolutePath());
     recorder.prepare();
recorder.start();

// Timely obtain sound decibels through MediaRecorder and convert them to toy intensity
        int ratio = recorder.getMaxAmplitude() / BASE;
            int db = 0;// decibels
            int realDb = 0;
            if (ratio > 1) {
               ......                              }
                  }
            }
            soundLevel = db;
            index++;
            if (index % 5 == 0) {
                index = 0;
                dbs.add(db);
                if (dbs.size() > maxCount) {
                    dbs.remove();
                }
            ......
                }
                order = order * 5 * (sensitivity + 100) / 100;// Set another sensitivity for intensity
                order = order > 100 ? 100 : order;
                order = order < 0 ? 0 : order;

order = order * (sensitivity) / 100; // percentage
                sendCommand(order); // Convert to corresponding instruction and send
            }
        } else {
            this.realDb = 0;
            soundLevel = 0;
        }
```

*Fig. 10*

SYSTEM, APPARATUS, AND METHOD FOR CONTROLLING DEVICES BASED ON SOUND

FIELD OF THE INVENTION

The present disclosure generally relates to a system, apparatus, and method for controlling devices, and more particularly to a system, apparatus, and method for controlling devices based on sound.

BACKGROUND OF THE INVENTION

Conventional control of adult toys typically involves direct control of these devices by a user. For example, these devices are typically controlled independently of an operation of a user device such as a phone or a tablet of the user or ambient conditions surrounding the user. Accordingly, conventional systems typically do not account for a sound of a user device or ambient conditions surrounding the user in controlling devices such as adult toys.

Accordingly, a need in the art exists for an efficient technique for controlling devices such as adult toys based on sounds of a user device and/or ambient conditions surrounding users of adult toys.

The exemplary disclosed system and method are directed to overcoming one or more of the shortcomings set forth above and/or other deficiencies in existing technology.

SUMMARY OF THE INVENTION

In one exemplary aspect, the present disclosure is directed to a system. The system includes an accessory control module, comprising computer-executable code stored in non-volatile memory, a processor, a device of a human user, and an accessory configured to communicate with the device, the accessory including a motor or a heater. The accessory control module, the processor, the device, and the accessory are configured to receive or obtain audio data using the device, identify at least one parameter of the audio data, the at least one parameter having one or more parameter values, convert the one or more parameter values into one or more action signals, and control the motor or the heater using the one or more action signals to perform a predefined act of the accessory at a parameter-dependent intensity synchronously with receiving or obtaining the audio data. The predefined act sexually stimulates the human user.

In another aspect, the present disclosure is directed to a method. The method includes providing a device of a human user, providing an accessory configured to communicate with the device, the accessory including a motor or a heater, receiving or obtaining audio data using the device, identifying at least one parameter of the audio data, the at least one parameter having one or more parameter values, converting the one or more parameter values into one or more action signals, and controlling the motor or the heater using the one or more action signals to perform a predefined act of the accessory at a parameter-dependent intensity synchronously with receiving or obtaining the audio data. The predefined act sexually stimulates the human user.

BRIEF DESCRIPTION OF THE DRAWINGS

FIG. 5 illustrates an exemplary implementation of the present invention;

FIG. 6 illustrates an exemplary implementation of the present invention;

FIG. 7 illustrates an exemplary implementation of the present invention;

FIG. 8 illustrates an exemplary implementation of the present invention;

FIG. 9 illustrates an exemplary implementation of the present invention;

FIG. 10 illustrates an exemplary implementation of the present invention;

DETAILED DESCRIPTION AND INDUSTRIAL APPLICABILITY

Figure 1:
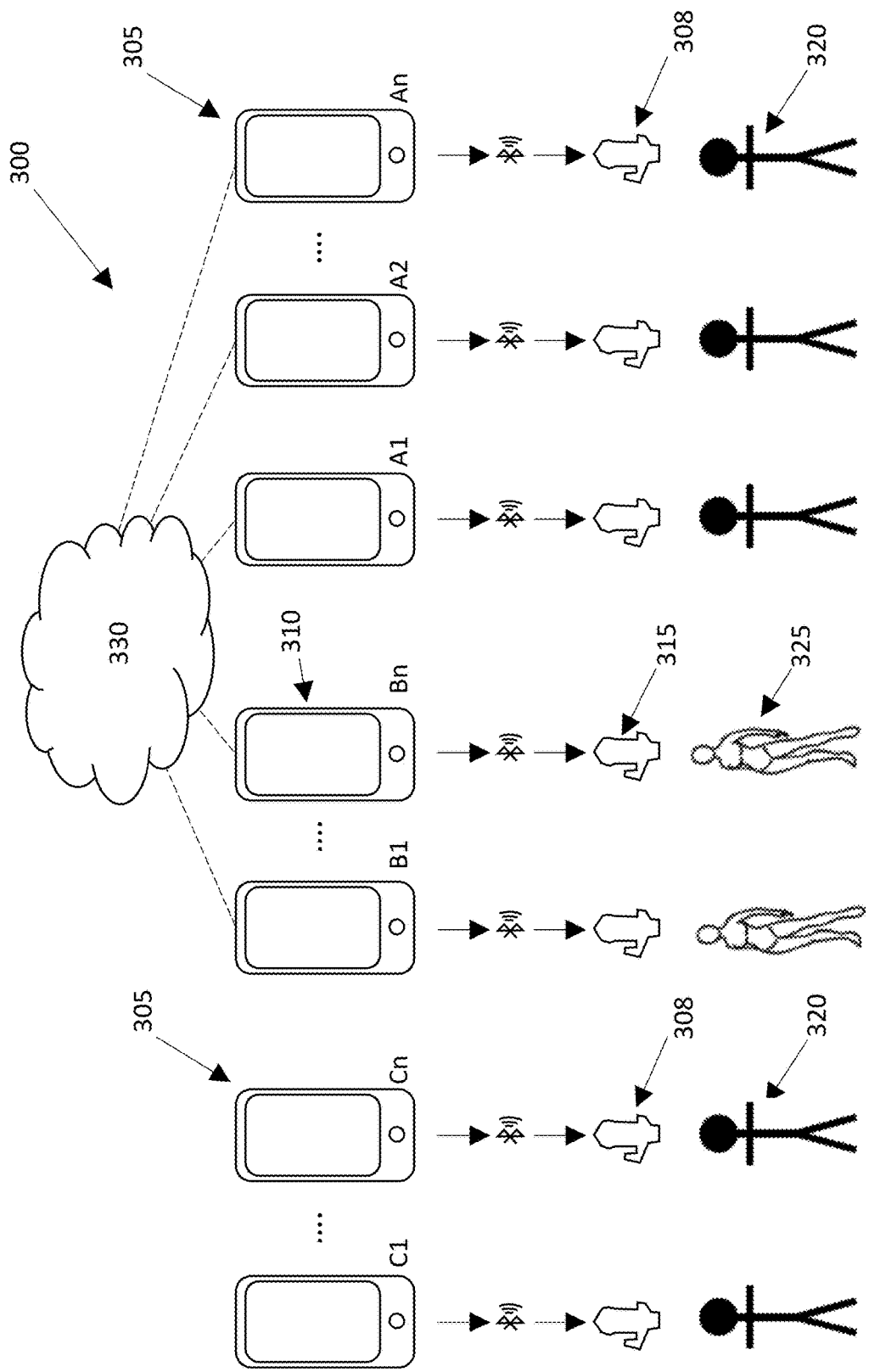
FIG. 1 is a schematic illustration of an exemplary system of the present invention.

FIG. 1 illustrates an exemplary system 300 for controlling devices based on sound. In at least some exemplary embodiments, system 300 may be a system for controlling devices synchronously in real-time (e.g., in real-time or in near real-time) based on sound for an adult entertainment application. The exemplary disclosed system, apparatus, and method may be an audio-based online adult entertainment system, apparatus, and method. The exemplary disclosed system, apparatus, and method may be a telecommunications system, apparatus, and method for adult entertainment.

As illustrated in FIG. 1, system 300 may include one or more user devices 305, one or more model devices 310, one or more user accessories 308, and one or more model accessories 315. For example, system 300 may include a plurality of user devices 305, a plurality of user accessories 308, a plurality of model devices 310, and a plurality of model accessories 315. Data such as image data, audio data, and/or control data may be transferred between user devices 305, user accessories 308, model devices 310, and model accessories 315.

As illustrated in FIG. 1, system 300 may include any desired number of user devices 305 (e.g., A1, A2, . . . An). User device 305 may be any suitable device for interfacing with other components of system 300 such as the exemplary disclosed accessories and/or other computing devices (e.g., user interface). For example, user device 305 may be any suitable user interface for receiving input and/or providing output (e.g., image data) to a user 320. User device 305 may include a camera and a microphone. User device 305 may be, for example, a touchscreen device (e.g., of a smartphone, a tablet, a smartboard, and/or any suitable computer device), a wearable device, a computer keyboard and monitor (e.g., desktop or laptop), an audio-based device for entering input and/or receiving output via sound, a tactile-based device for entering input and receiving output based on touch or feel, a dedicated user interface designed to work specifically with other components of system 300, and/or any other suitable user interface (e.g., including components and/or configured to work with components described below regarding FIGS.

11 and 12). For example, user device 305 may include a touchscreen device of a smartphone or handheld tablet. For example, user device 305 may include a display (e.g., a computing device display, a touchscreen display, and/or any other suitable type of display) that may provide output, image data, and/or any other desired output or input prompt to a user. For example, the exemplary display may include a graphical user interface to facilitate entry of input by a user and/or receiving output such as image data. An application for example as described herein and/or a web browser may be installed on user device 305 and utilized by user 320. Model device 310 may be similar to user device 305.

Figure 2:
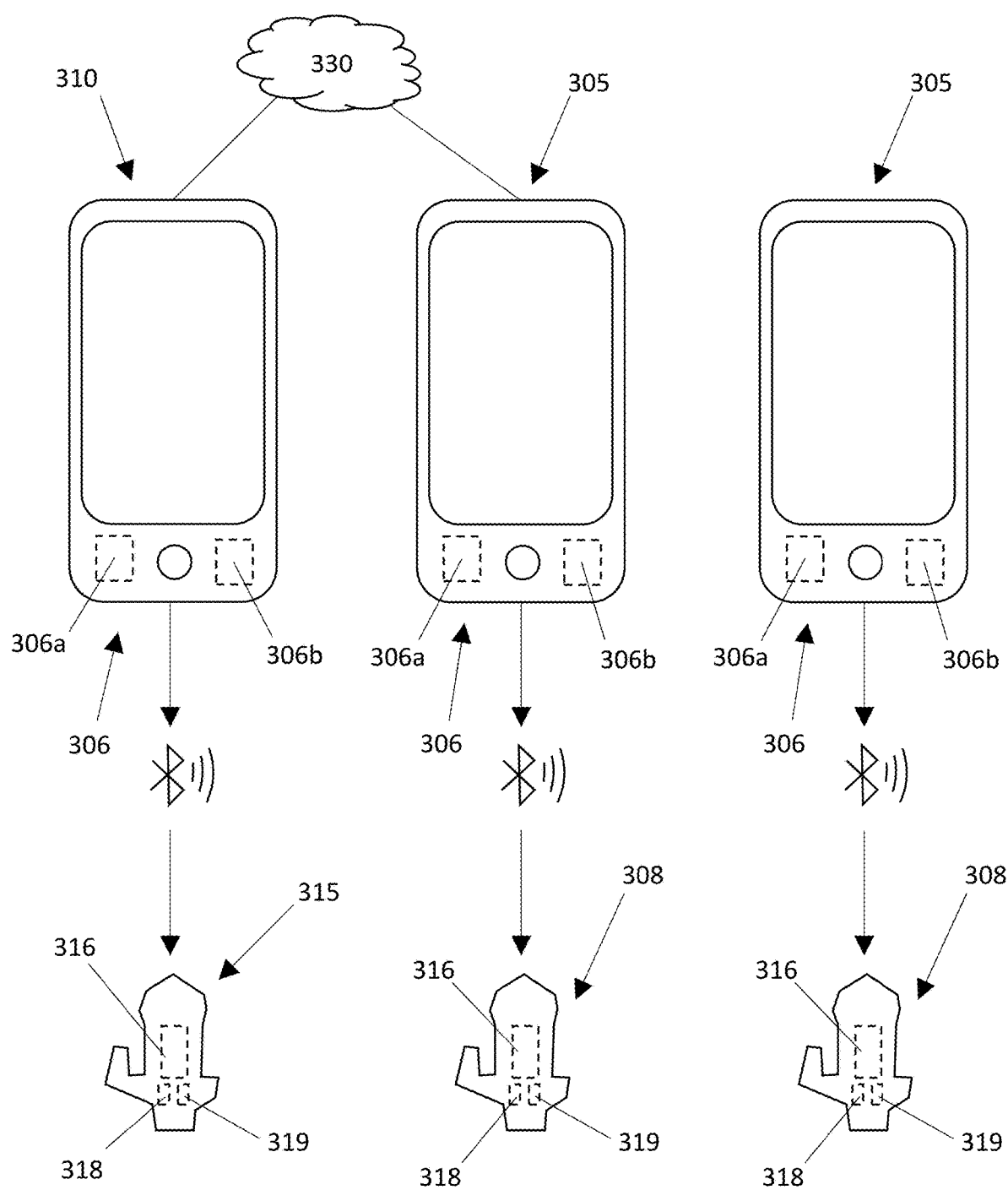
FIG. 2 is a schematic illustration of an exemplary system of the present invention.

As illustrated in FIG. 2, user device 305 may include a sensor array 306. In at least some exemplary embodiments, sensor array 306 may include one or more sensors integrated or built into the exemplary disclosed user device (e.g., user device 305) such as, for example, a mobile phone, a pad, or a wearable device. Sensor array 306 may also include an audio sensor (e.g., a microphone) for sensing, detecting, and recording ambient or nearby noise or sound. For example, sensor array 306 may operate to detect and/or record noise or sound at a location of user device 305. Sensor array 306 may include any suitable sensors for use with system 300 such as, for example, a location sensor 306a and a movement sensor 306b. Location sensor 306a may include a GPS device, a Galileo device, a GLONASS device, an IRNSS device, a BeiDou device, and/or any other suitable device that may operate with a global navigation system.

Movement sensor 306b may include any suitable components for sensing motion (e.g., motion amplitude), velocity, and/or acceleration. Movement sensor 306b may include an acceleration sensor. Movement sensor 306b may include a gyroscope. For example, movement sensor 306b may include a displacement sensor, a velocity sensor, and/or an accelerometer. For example, movement sensor 306b may include components such as a servo accelerometer, a piezoelectric accelerometer, a potentiometric accelerometer, and/or a strain gauge accelerometer. Movement sensor 306b may include a piezoelectric velocity sensor or any other suitable type of velocity or acceleration sensor.

System 300 may include any desired number of model devices 310 (e.g., B1 . . . Bn). Model device 310 may be similar to user device 305. For example, model device 310 may include any suitable user interface for receiving input and/or providing output (e.g., image data) for a model 325. Model 325 may operate model device 310 to record and transfer image (e.g., video) and audio data to one or more users 320 via a network 330. One or more models 325 may use respective model devices 310 to communicate with one or more users 320 using respective user devices 305 via network 330 or directly.

Model accessory 315 may be any suitable accessory for use by model 325 (e.g., when model 325 is imaged by model device 310). For example, model accessory 315 may be a prop that is used by model 325 while model 325 is being imaged (e.g., a video or pictures of model 325 are being recorded and/or transmitted for example via model device 310 synchronously in real-time to be viewed by user 320). For example, model accessory 315 may be a device used for erotic stimulation (e.g., a sex aid or a "sex toy"). Model accessory 315 may be a sexual simulation device that may be associated with a given model 325 and respective model device 310 of that given model 325. In at least some exemplary embodiments, model accessory 315 may be a massaging apparatus for human genitalia (e.g., a vibrator). For example, model accessory 315 may be any suitable device for use in a video or pictures recorded by model device 310, which may be an erotic video or erotic pictures). In at least some exemplary embodiments, model accessory 315 may be a tool or other indicator that may be used in video or pictures recorded by model device 310 such as surveying equipment, a sign providing information such as location or time information, a surveillance tool used by model 325, and/or any other suitable tool or accessory that may be used while model device 310 is recording a video or pictures of model 325. For example, model 325 may be an erotic model using model accessory 315 that may be an erotic device, a technician or laborer using model accessory 315 that may be a tool or work device specific to a desired application, an operative using model accessory 315 that may be a surveillance tool or a part of a weapon system being recorded by model device 310, and/or any other desired role using any suitable model accessory 315.

Model accessory 315 may include a motor 316. Motor 316 may include an electric motor. Motor 316 may include a server motor, a stepper motor, a brushless motor, or any other suitable type of motor. Motor 316 may include any suitable vibration motor or haptic motor such as, for example, a mini vibrator motor. Motor 316 may include a low voltage motor. Motor 316 may include a pager motor or a coin vibration motor. Motor 316 may include a linear resonant actuator or an eccentric rotating mass vibration motor. Motor 316 may be powered by any suitable power source, such as a battery (e.g., a nickel-metal hydride battery, a lithium-ion battery, an ultracapacitor battery, a lead-acid battery, and/or a nickel cadmium battery), an electric power source (e.g., a transformer connected to a plug that may plug into an outlet), and/or any other suitable energy source. Model accessory 315 may include a controller 319 that may be any suitable computing device for controlling an operation of motor 316 and a communication device 318. Controller 319 may, for example, include components similar to the components described below regarding FIG. 11. Controller 319 may include for example a processor (e.g., micro-processing logic control device) or board components. Controller 319 may control motor 316 based on input data and/or commands received from user device 305 and/or model device 310 via network 330 and/or a communication device 318 (e.g., transferred directly to communication device 318 by any suitable component of system 300). Motor 316 may be controlled by controller 319 to vibrate model accessory 315 at a desired level or strength, perform a suction operation at a desired level or strength using model accessory 315 (e.g., using model accessory 315 as a suction device), rotate or swing model accessory 315 at a desired speed or amount, contract or expand model accessory 315 by a desired amount, cause model accessory 315 to perform an inhalation action, and/or cause model accessory 315 to perform any other suitable action or function.

In at least some exemplary embodiments, motor 316 may be or may include a thermal device such as a heater. In at least some exemplary embodiments, motor 316 may include an electric heating device such as an electric resistance heating device or any other suitable heating or cooling device. Motor 316 may include a polyimide heater, a silicone rubber heater, and/or a resistive wire heater. Motor 316 may be controlled by controller 319 to heat or emit heat or warmth from model accessory 315. For example, motor 316 may cause a temperature variation of model accessory 315.

User accessory 308 may be similar to model accessory 315. User accessory 308 may be a sexual simulation device that may be associated with a given user 320 (e.g., a viewer of one or more models 325) and respective user device 305 (e.g., a viewer device) of that given user 320. A given user 320 may operate a given user accessory 308 similarly to as described above regarding an operation of a given model accessory 315 by a given model 325.

Network 330 may be any suitable communication network over which data may be transferred between one or more user devices 305, one or more user accessories 308, one or more model devices 310, and/or one or more model accessories 315. Network 330 may be the internet, a LAN (e.g., via Ethernet LAN), a WAN, a WiFi network, or any other suitable network. Network 330 may be similar to WAN 201 described below. The components of system 300 may also be directly connected (e.g., by wire, cable, USB connection, and/or any other suitable electro-mechanical connection) to each other and/or connected via network 330. For example, components of system 300 may wirelessly transmit data by any suitable technique such as, e.g., wirelessly transmitting data via 4G LTE networks (e.g., or 5G networks) or any other suitable data transmission technique for example via network communication. Components of system 300 may transfer data via the exemplary techniques described below regarding FIG. 12. User devices 305, user accessories 308, model devices 310, and/or model accessories 315 may include any suitable communication components for communicating with other components of system 300 using for example the communication techniques described above. For example, user devices 305 and model devices 310 may include integrally formed communication devices (e.g., smartphone components), and user accessories 308 and model accessories 315 may each include communication device 318 that may communicate using any of the exemplary disclosed communication techniques.

In at least some exemplary embodiments, a given model accessory 315 may communicate with a given model device 310 (e.g., a paired model device 310) via any suitable short distance communication technique. For example, model accessories 315 (e.g., via communication device 318) and model devices 310 may communicate via WiFi, Bluetooth, ZigBee, NFC, IrDA, and/or any other suitable short distance technique. Model accessory 315 may be an adult toy that may be connected with model device 310 through short distance wireless communication. An application (e.g., operating using the exemplary disclosed modules) may be installed on model device 310, the application and model device 310 being configured to send commands to model accessory 315 to drive (e.g., actuate) model accessory 315. User accessory 308 may communicate with user device 305 similarly to the communication of model accessory 315 and model device 310 described above.

In at least some exemplary embodiments, user accessory 308 may operate with and communicate with user device 305, and model accessory 315 may operate with and communicate directly with model device 310, independently of network 330. For example as illustrated in FIG. 1, any desired number of user devices 305 (e.g., C1 ... Cn) may be in an offline mode that may be disconnected from network 330 while communicating with respective user accessories 308. Model devices 310 and model accessories 315 may similarly operate in an offline mode.

System 300 may include one or modules for performing the exemplary disclosed operations. The one or more modules may include an accessory control module for controlling user accessory 308 and model accessory 315. The one or more modules may be stored and operated by any suitable components of system 300 (e.g., including processor components) such as, for example, network 330, user device 305, user accessory 308, model device 310, model accessory 315, and/or any other suitable component of system 300. For example, system 300 may include one or more modules having computer-executable code stored in non-volatile memory. System 300 may also include one or more storages (e.g., buffer storages) that may include components similar to the exemplary disclosed computing device and network components described below regarding FIGS. 11 and 12. For example, the exemplary disclosed buffer storage may include components similar to the exemplary storage medium and RAM described below regarding FIG. 11. The exemplary disclosed buffer storage may be implemented in software and/or a fixed memory location in hardware of system 300. The exemplary disclosed buffer storage (e.g., a data buffer) may store data temporarily during an operation of system 300.

Figure 3:
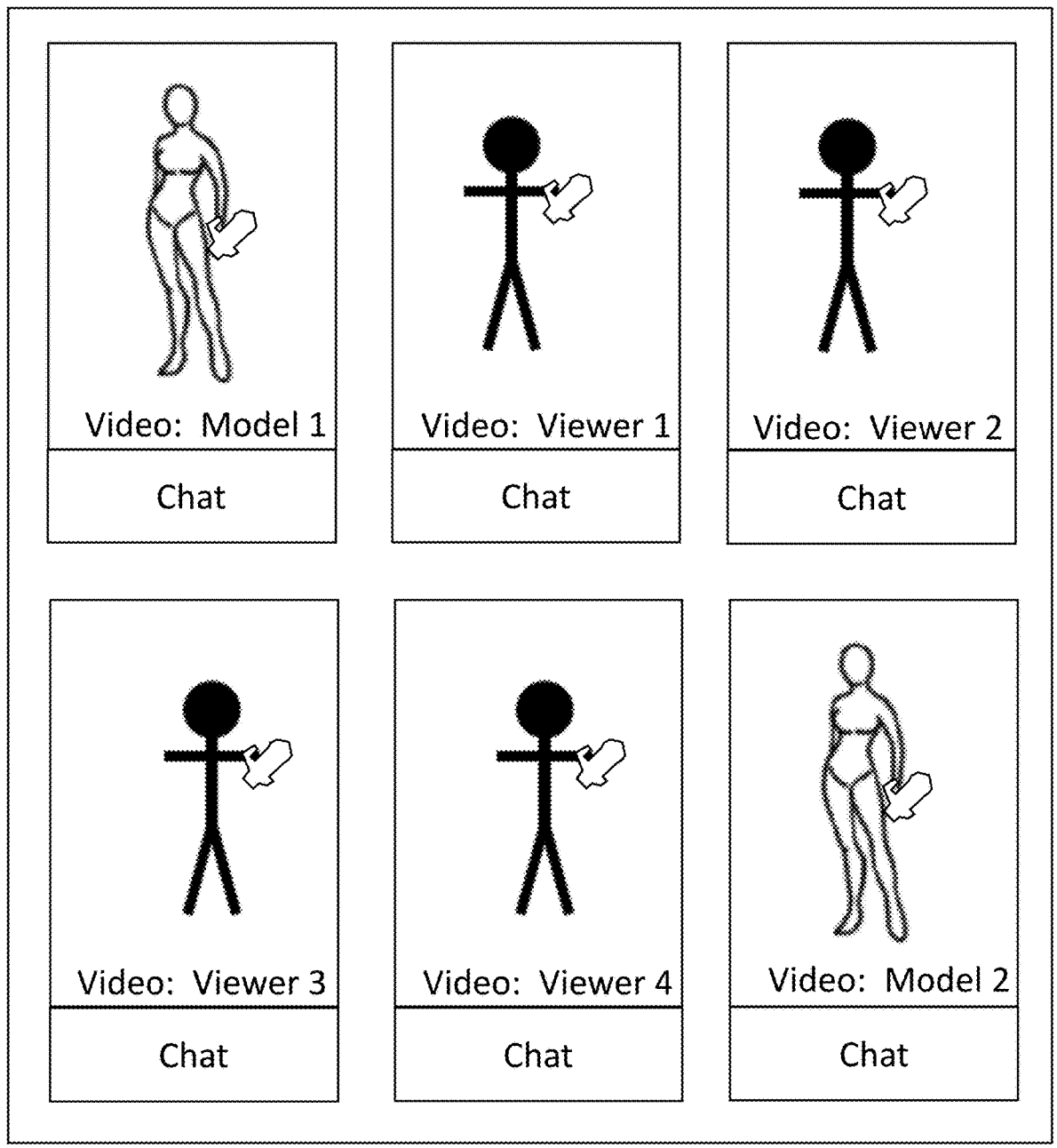
FIG. 3 is a schematic illustration of an exemplary system of the present invention.

The one or more exemplary disclosed modules may also provide a chat room interface via user device 305 and model device 310 for use by each user 320 and model 325. For example, video display of model 325, one or more users 320, and/or and a chat or messaging app (e.g., any suitable chat communication or messaging app such as, for example, text, voice, and/or video chat boxes) may be displayed to each user 320 via user device 305 and to each model 325 via model device 310. One or more users 320 and one or more models 325 may thereby view and chat (e.g., text, voice, and/or video chat) with each other via the one or more exemplary disclosed modules via respective user devices 305 and model devices 310. Each user 320 may thereby view, interact with, and/or chat (e.g., text, voice, and/or video chat) with one or more models 325 and/or other users 320. Also, each model 325 may thereby view, interact with, and/or chat with one or users 320 and/or other models 325. For example, multiple text, voice, and/or video chat boxes including a plurality of users 320 (e.g., viewers each having one or more user accessories 308) and/or a plurality of models 325 (e.g., each having one or more model accessories 315) may be displayed to each user 320 and each model 325 via respective user devices 305 and model devices 310. Users 320 and models 325 may thereby view and interact with other users 320 and models 325 that may each have one or more respective accessories (e.g., respective user accessories 308 and model accessories 315). FIG. 3 schematically illustrates an exemplary embodiment of the exemplary disclosed chat room that may be displayed to user 320 via user device 305 or to model 325 via model device 310.

The exemplary disclosed system, apparatus, and method may be used in any suitable application for controlling a device based on sound. For example, the exemplary disclosed system, apparatus, and method may be used in any suitable application for controlling a device based on music. The exemplary disclosed system, apparatus, and method may be used in any suitable application for controlling a device based on sound provided by a user device of a user such as online music or audio (e.g., sound), locally stored music or audio (e.g., sound), and/or ambient sound at a location of the user. The exemplary disclosed system, apparatus, and method may be used in any suitable application for controlling an adult toy.

Figure 4:
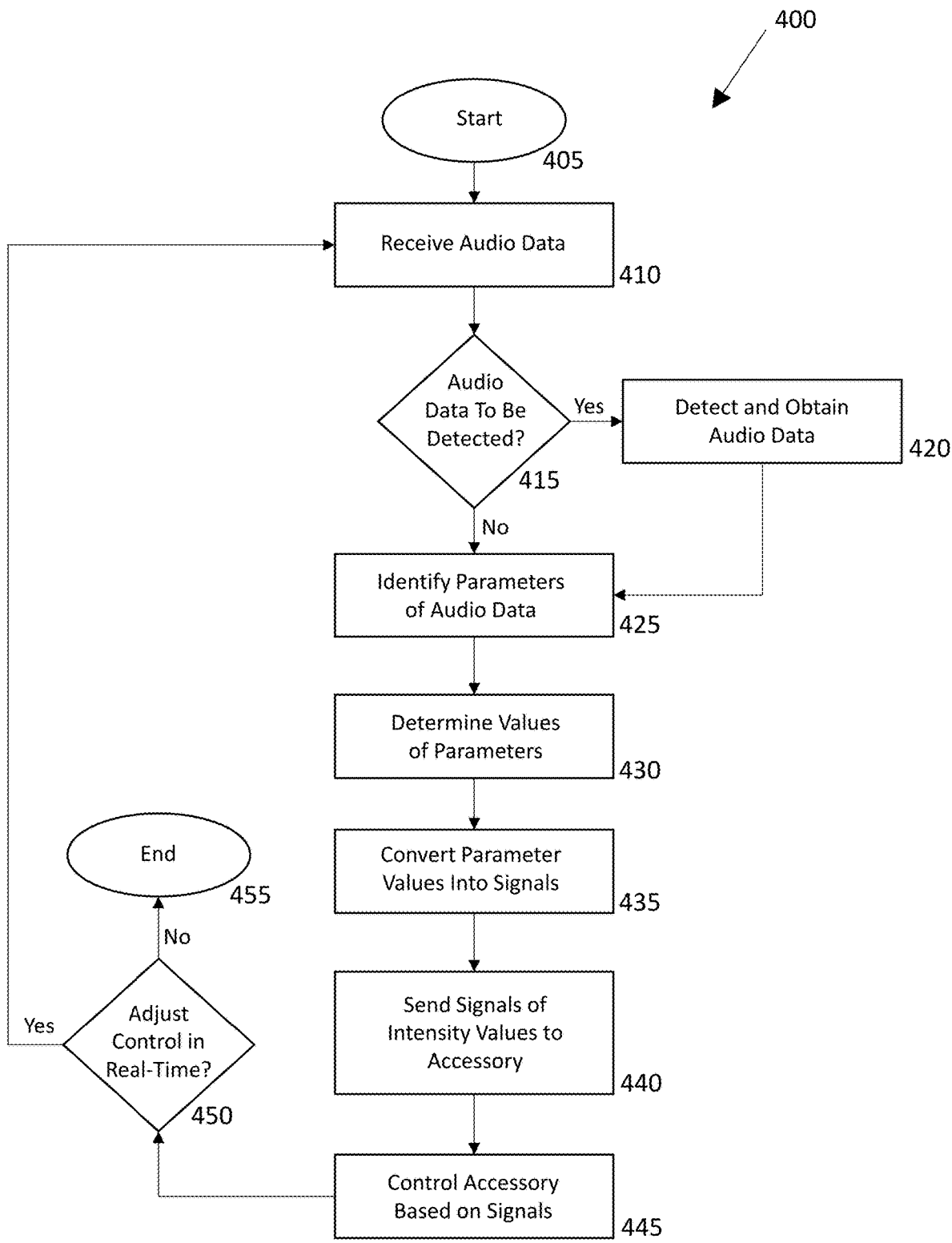
FIG. 4 is a flowchart showing an exemplary process of the present invention.

The exemplary disclosed system, apparatus, and method may receive or generate audio data, determine parameters of the audio data, convert the parameters into signals, and control a device to operate at a desired intensity (e.g., amplitude) using the signals. An exemplary operation of the exemplary disclosed system, apparatus, and method will now be described. FIG. 4 illustrates an exemplary process 400 of system 300. Process 400 begins at step 405.

At step 410, user device 305 and/or model device 310 may receive audio data. For example, user device 305 and/or model device 310 may receive audio data (e.g., music and/or any other suitable audio or sound data) online (e.g., A1, A2, . . . An and/or B1 . . . Bn). For example, audio data may be transferred via network 330 to one or more user devices 305 and/or model devices 310. For example, audio data may be received by user device 305 and/or model device 310 based on online music such as from an online music player (e.g., Spotify, Youtube, Pandora, and/or any other suitable source). The audio data may be transferred (e.g., streamed) synchronously in real-time or near real-time to user device 305 and/or model device 310 (e.g., relative to the other exemplary disclosed steps of process 400). For example, the audio data may be transferred synchronously in real-time or near real-time to participants of the exemplary disclosed chat room (e.g., as illustrated in FIG. 3) via their respective user devices 305 and/or model devices 310. The audio data may also be stored on (e.g., downloaded and stored on) local storage of user device 305 and/or model device 310 (e.g., C1 . . . Cn).

At step 415, system 300 may determine whether or not audio data is detected. If audio data is not detected or is not to be detected, process 400 may proceed to step 425. If audio data is detected or is to be detected, process 400 may proceed to step 420.

At step 420, user device 305 and/or model device 310 may detect and/or record ambient sound (e.g., nearby or surrounding sound) at a location of the user. For example, the exemplary disclosed audio sensor (e.g., microphone of sensor array 306) may operate to detect and/or record noise or sound at a location of user device 305 and/or model device 310. User device 305 and/or model device 310 may be controlled by respective user 320 and/or model 325 to detect and/or record noise or sound and/or may detect and/or record noise based on predetermined algorithms, criteria, conditions, and/or any other suitable criteria. For example, user device 305 and/or model device 310 may identify, detect, and/or record sound synchronously in real-time or near real-time (e.g., relative to the other exemplary disclosed steps of process 400) that may originate from surroundings (e.g., ambient noise, sound, such as from people, music, or game scenes of a device such as a video game player). For example, user device 305 and/or model device 310 may identify, detect, and/or record sound falling into predetermined ranges of amplitude, period, frequency, pitch, timbre, volume, speed, decibels, and/or any other suitable criteria. Process 400 may then proceed to step 425.

At step 425, system 300 may identify parameters of the audio data received at step 410 and/or detected and obtained at step 420. System 300 may identify the parameters of the audio data based on input provided by users 320 and/or models 325, predetermined algorithms or criteria based on the exemplary disclosed operation of system 300, machine learning for example as described herein, and/or any other suitable criteria. The exemplary disclosed parameters may include amplitude, period, frequency, pitch, timbre, volume, speed, decibels, and/or any other suitable characteristics of the audio data.

At step 430, system 300 may determine values of the exemplary disclosed parameters. For example, system 300 may decompose a data file of the audio data, and obtain data or values of the exemplary disclosed parameters. System 300 may decompose a data file of the audio data synchronously in real-time or near real-time (e.g., relative to the other exemplary disclosed steps of process 400). System 300 may determine values of amplitude, period, frequency, pitch, timbre, volume, speed, decibels, and/or any other suitable parameters of the audio data. For example, system 300 may determine a volume of the audio data based on how loudly the audio data is played or is to be played. The values determined based on the data received or obtained by system 300 at steps 410 and/or 420 may correspond to (e.g., be proportional to) an intensity value described below at step 440.

At step 435, system 300 may convert parameter values determined at step 430 into signals for controlling one or more user accessories 308 and/or model accessories 315. For example, system 300 may utilize one or more predetermined (e.g., preset) algorithms to convert one or more parameters identified at step 425 (e.g., designated parameters) of the audio data received and/or obtained at steps 410 and/or 420 into one or more action signals based on parameter values determined at step 430. The one or more parameter values may be converted into one or more parameter-dependent intensities (e.g., motion amplitudes or other actions) for user accessory 308 and/or model accessory 315 (e.g., a sexual stimulation device) to perform a predefined act. The parameter-dependent intensities may be based on the one or more parameter values, and may change at any time (e.g., based on a change of the one or more parameter values).

System 300 may convert parameter values determined at step 430 into signals (e.g., action signals) having intensity values for controlling one or more user accessories 308 and/or model accessories 315 that may be proportional (e.g., or inversely proportional) to the parameter values. For example, as a given parameter value increases, a given corresponding signal intensity value may increase. As a given parameter value decreases, a given corresponding signal intensity value may decrease. As described below regarding step 445, the exemplary disclosed signals (e.g., action signals) may control one or more user accessories 308 and/or model accessories 315 to perform actions. The parameter values may be proportional to the action signals that may control one or more user accessories 308 and/or model accessories 315 to perform predefined acts for example as described below regarding step 445.

FIGS. 5-10 illustrate exemplary embodiments of the exemplary disclosed algorithms for converting parameter values determined at step 430 into signals for controlling one or more user accessories 308 and/or model accessories 315. The exemplary disclosed algorithms may be algorithms for use with iOS, Android, and/or any other suitable operating system. For example, FIGS. 5-7 illustrate exemplary algorithms for use with iOS and FIGS. 8-10 illustrate exemplary algorithms for use with Android. FIGS. 5 and 8 illustrate algorithms for use with receiving local audio data (e.g., locally stored music) for example as described above at step 410. FIGS. 6 and 9 illustrate algorithms for use with receiving online audio data (e.g., internet streaming) for example as described above at step 410. FIGS. 7 and 10 illustrate algorithms for use with detecting and obtaining sound at a location of user device 305 and/or model device 310 for example as described above at step 420. At step 435, one or more of the exemplary disclosed algorithms for example as illustrated at FIGS. 5-10 may convert the exemplary disclosed parameter values into action signals having signal intensity values that may be proportional to the converted parameter values.

For example as illustrated in FIGS. 8-10, the exemplary disclosed system, apparatus, and method may involve playback devices on an Android platform for music and/or sound. For locally stored sound or music (e.g., local music) for example as illustrated in FIG. 8, the exemplary disclosed algorithm may include obtaining the sound of the Media- Player player through Record_Audio. The exemplary disclosed algorithm may also include playing the local music through MediaPlayer to obtain the corresponding getAudioSessionId. The exemplary disclosed algorithm may additionally include obtaining the corresponding visualizer through the sessionId to obtain the music spectrum.

For online sound or music (e.g., online music) for example as illustrated in FIG. 9, the exemplary disclosed algorithm may include obtaining music of a player (e.g., an online player such as Spotify or other player for example as described herein) by using an SDK (e.g., the Spotify SDK) to obtain the sessionId of the playback application. The exemplary disclosed algorithm may also include obtaining the visualizer through the sessionId to obtain the music spectrum. The exemplary disclosed algorithms may use the sessionId to obtain the visualizer spectrum, with the technique for obtaining the sessionId being different between some algorithms in at least some exemplary embodiments.

For example as illustrated in FIGS. 8 and 9, after acquiring the frequency spectrum, the built-in FFT function of the Android system may perform audio analysis to obtain the amplitude of the music. For example through the algorithm formulas set forth in FIGS. 8 and 9, the amplitude of the music may be converted into the driving command of the vibration intensity of the sexual stimulation device synchronously in real-time or near real-time (e.g., relative to the other exemplary disclosed steps of process 400).

For example as illustrated in FIG. 10 for ambient or nearby noise or sound at a location of user device 305 or model device 310 (e.g., that may include an Android platform), the sound may be detected by the exemplary disclosed audio sensor (e.g., microphone) of user device 305 or model device 310. The decibel value of the microphone may be periodically taken through the MediaRecorder, and then through the algorithm formulas for example as set forth in FIG. 10. The decibel value of the sound may be converted into the exemplary action signals corresponding to signal intensity values (e.g., the driving instruction of the action intensity such as vibration intensity of the exemplary disclosed accessory such as a sexual stimulation device) synchronously in real-time or near real-time (e.g., relative to the other exemplary disclosed steps of process 400).

Also for example as illustrated in FIGS. 5-7, the exemplary disclosed system, apparatus, and method may involve playback devices on an iOS platform for music and/or sound. The exemplary disclosed algorithms involving an iOS platform may utilize audio conversion algorithms that may be generally similar to the exemplary disclosed algorithms for the Android platform described above. For locally stored and online music and sound for example as illustrated in FIGS. 5 and 6, AVAudioPlayer may obtain the channel information in the music. For ambient or nearby noise or sound at a location of user device 305 or model device 310 for example as illustrated in FIG. 7, AVAudioRecorder may obtain (e.g., and pass) the channel information based on an operation of the exemplary disclosed audio sensor (e.g., microphone). The value of the sound channel may be converted into the action signal corresponding to a signal intensity value (e.g., the driving instruction of the action intensity such as vibration intensity of the exemplary disclosed accessory such as a sexual stimulation device) synchronously in real-time or near real-time (e.g., relative to the other exemplary disclosed steps of process 400). In at least some exemplary embodiments and as illustrated in FIG. 7, the exemplary disclosed algorithm may include: open func averagePower(forChannel channelNumber: Int)→Float/* returns average power in decibels for a given channel*/

At step 440, system 300 may transfer the exemplary disclosed action signals corresponding to signal intensity values, which may be converted at step 435 from parameter values, to the exemplary disclosed accessory (e.g., user accessory 308 or model accessory 315). For example, user devices 305 or model devices 310 may transfer (e.g., send) the exemplary disclosed action signals corresponding to signal intensity values to respective user accessories 308 or model accessory 315 via the exemplary disclosed communication techniques. The data may be transferred from user device 305 or model device 310 to controller 319 of respective user accessory 308 or model accessory 315 via communication device 318.

At step 445, system 300 may control an operation of one or more user accessories 308 and/or model accessories 315 based on the exemplary disclosed signal intensity values sent at step 440. Controller 319 may control motor 316 of user accessory 308 or model accessory 315 to perform one or more actions at a parameter-dependent intensity (e.g., desired level or intensity) based on a value of signal intensity values corresponding to the action signals. For example, the action signals may correspond to signal intensity values for an operation of motor 316. Based on the action signals received and transferred by communication device 318, controller 319 may control motor 316 to operate at a desired intensity based on signal intensity values corresponding to the action signals and determined by system 300 (e.g., by controller 319). Controller 319 may control motor 316 to perform one or more predefined acts at one or more parameter-dependent intensities (e.g., levels) based on the signal intensity values. The parameter-dependent intensities may be based on the one or more parameter values, and may change at any time (e.g., based on a change of the one or more parameter values). The parameter-dependent intensities may vary proportionally to a change of the one or more parameter values.

In at least some exemplary embodiments, the predefined act may include one or more of the accessory (e.g., user accessory 308 or model accessory 315) vibrating, performing a suction operation (e.g., the accessory acting as a suction device), rotating or swinging, contracting or expanding, increasing or decreasing in temperature (e.g., heating, cooling, and/or undergoing temperature variation), performing an inhalation action, and/or any other suitable action or function. The predefined act may be based on the action signals and corresponding signal intensity values, which may correspond to and be proportional to the parameter values. A level or intensity of the predefined act may also be based on the action signals and corresponding signal intensity values. Predefined acts and/or levels or intensities may be based on various ranges of parameter values for the exemplary disclosed parameters. For example, predefined acts and/or levels or intensities may be based on ranges of preset sensitivities of the parameter values. Also for example, predefined acts and/or levels or intensities may be based on one or more designated frequency bands of the parameter values. Controller 319 may control motor 316 to operate at a relatively higher or lower level or intensity based on the signal intensity values corresponding to the action signals. The predefined act performed at a parameter-dependent intensity (e.g., level) based on the signal intensity values corresponding to the action signals may include one or more of the accessory (e.g., user accessory 308 or model accessory 315) vibrating at a desired level or strength, performing a suction operation at a desired level or strength (e.g., the accessory acting as a suction device), rotating or swinging at a desired speed or amount (e.g., desired motion amplitude), contracting or expanding by a desired amount, increasing or decreasing in temperature by a desired amount of temperature (e.g., heating, cooling, and/or undergoing temperature variation), performing an inhalation action at a desired level, and/or any other suitable action or function at any desired level or intensity. For example as the exemplary disclosed parameter values of sound or music received or obtained at steps 410 and 420 increases (e.g., amplitude, period, frequency, pitch, timbre, volume, speed, decibels, and/or any other suitable characteristics increase), a level or intensity of the one or more exemplary disclosed predefined acts may increase synchronously in real-time or near real-time. As the exemplary disclosed parameter values of sound or music received or obtained at steps 410 and 420 decreases (e.g., amplitude, period, frequency, pitch, timbre, volume, speed, decibels, and/or any other suitable characteristics decrease), a level or intensity of the one or more exemplary disclosed predefined acts may decrease synchronously in real-time or near real-time.

In at least some exemplary embodiments, the audio data may be of music or any other suitable sound that may include portions that may vary in a rhythmic or repetitive manner. As the parameter values vary based on the rhythmic or repetitive portions of the audio data, the predefined act performed by the exemplary disclosed accessory (e.g., user accessory 308 or model accessory 315) may also vary in a rhythmic or repetitive manner synchronously in real-time or near real-time to sexually stimulate user 320 or model 325.

The exemplary disclosed parameter values, action signals and corresponding signal intensity values, and parameter-dependent intensities (e.g., levels) may be proportionally related (e.g., or inversely proportionally related). For example, as a given parameter value increases, a corresponding action signal and signal intensity value may increase, causing controller 319 to control motor 316 to operate at an increased level or intensity so that the exemplary disclosed accessory (e.g., user accessory 308 or model accessory 315) performs one or more exemplary predefined acts at a relatively increased level or intensity. As a given parameter value decreases, a corresponding action signal and signal intensity value may decrease, causing controller 319 to control motor 316 to operate at a decreased level or intensity so that the exemplary disclosed accessory (e.g., user accessory 308 or model accessory 315) performs one or more exemplary predefined acts at a relatively decreased level or intensity. Controller 319 may control motor 316 to operate so that the exemplary disclosed accessory (e.g., user accessory 308 or model accessory 315) performs one or more of the exemplary disclosed predefined acts at one or more of the exemplary disclosed parameter-dependent intensities (e.g., levels) based on the parameter values and action signals and corresponding signal intensity values (e.g., synchronously in real-time or near real-time). For example, based on parameter values identified and determined at steps 425 and 430, system 300 may convert the parameter values into action signals and control the exemplary disclosed accessories based on the signal intensity values synchronously in real-time or near real-time as sound or music is received or obtained at steps 410 and 420. System 300 may thereby perform the exemplary disclosed steps of process 400 synchronously in real-time or near real-time with each other. In at least some exemplary embodiments, users 320 and/or models 325 communicating with each other via the exemplary disclosed chat room (e.g., as illustrated in FIG. 3) may view each other using and interacting with the exemplary disclosed accessories (e.g., user accessories 308 or model accessories 315) synchronously in real-time or near real-time.

At step 450, system 300 may determine whether an operation of user accessory 308 or model accessory 315 is to be adjusted synchronously in real-time or near real-time relative to sound or music being received or obtained. System 300 may control the exemplary disclosed accessory to automatically operate at a higher level or intensity when the exemplary parameter values increase, and may control the exemplary disclosed accessory to automatically operate at a lower level or intensity when the exemplary parameter values decrease. For example as the exemplary disclosed parameter values of sound or music received or obtained at steps 410 and 420 increases or decreases (e.g., amplitude, period, frequency, pitch, timbre, volume, speed, decibels, and/or any other suitable characteristics increase or decrease), a level or intensity of the one or more exemplary disclosed predefined acts may increase or decrease synchronously in real-time or near real-time. System 300 may also adjust an operation of user accessory 308 or model accessory 315 based on predetermined algorithms or criteria, user input, whether one or more users 320 has provided rewards or tips (e.g., payment such as virtual currency) to models 325, and/or any other suitable criteria. If an adjustment is to be made, process 400 returns to step 410 and steps 410 through 450 may be repeated for as many iterations as desired. If an adjustment is not to be made, if no sound or music is received at steps 410 and 420, and/or if further operation is not desired, process 400 may end at step 455.

In at least some exemplary embodiments, the exemplary disclosed system may associate a tipping signal of a human user (e.g., one or more users 320 and/or one or more models 325) with an activation command of an audio control function (e.g., in advance). For example, the exemplary disclosed system may associate the tipping signal with a predetermined audio control or operation (e.g., to provide a sound that may be perceived as rewarding or encouraging to a user). When receiving the tipping signal of the human user, the exemplary disclosed system may activate the activation command to provide the audio control function to the human user.

In at least some exemplary embodiments, the exemplary disclosed system may be an audio-based online adult entertainment system including an operable sexual stimulation device configured to receive signals, a memory having stored thereon instructions, and a processor to execute said instructions resulting in a software application. The system may be configured to, based on one or more parameters of the audio, provide one or more signals that actuate the sexual stimulation device to perform a predefined act to sexually stimulate the users associated with the sexual stimulation device. The one or more signals may be used to actuate the sexual stimulation device to perform one or more motion amplitudes of the predefined act. The predefined act may include any one or a combination of vibration, rotation, swing, inhalation, temperature variation, expansion, suction, and contraction. The system may operate so that the greater the value of the audio parameter, the greater the motion amplitude of the sexual stimulation device performing the predefined act may be. A preset algorithm may be configured to convert one or more designated parameters of the audio into the one or more signals. The system may operate using a preset sensitivity of one or more ranges. The system may determine (e.g., calculate) one or more new motion amplitudes based on the preset sensitivity, and control (e.g., actuate) the sexual stimulation device to perform one or more new motion amplitudes of the predefined acts to sexually stimulate the user (e.g., or users) associated with the sexual stimulation device (e.g., or devices). The audio may include music played synchronously in real-time or near real-time, any other sound detected in real-time or near real-time, music that has been recorded (e.g., stored as data) but not played (e.g., not yet played), and/or any other sound that has been recorded but not played. When the audio includes music played synchronously in real-time or near real-time and/or any other sound detected synchronously in real-time or near real-time, the system may decompose the data file of the audio synchronously in real-time or near real-time, obtain one or more parameters in the data file, and actuate the sexual stimulation device to perform one or more motion amplitudes of the predefined acts to sexually stimulate the user associated with the sexual stimulation device. When the audio includes music or other sound that has been recorded but not played, the system may decompose the data file of the audio and obtain one or more parameters in the data file. The one or more parameters may be converted into one or more motion amplitudes for the sexual stimulation device to perform a predefined act. The system may acquire one or more designated frequency bands of the audio, and generate one or more signals that drive the sexual stimulation device to perform the predefined acts based on the one or more designated frequency bands, to stimulate the user associated with the sexual stimulation device. The frequency band may be a collection of frequencies within a certain range.

In at least some exemplary embodiments, the exemplary disclosed system may include a user device connected to the sexual stimulation device via Bluetooth or WiFi, wherein an application may be installed on the user device. The application may be configured to send commands to the sexual stimulation device to actuate the sexual stimulation device.

In at least some exemplary embodiments, the exemplary disclosed method may be an audio-based online entertainment method. The method may include decomposing the data file of the audio in real time, and obtaining one or more parameters in the data file. The audio may be music played synchronously in real-time or near real-time, or any other sound detected synchronously in real-time or near real-time. One or more signals that may actuate the sexual stimulation device to perform a predefined act may be generated synchronously (e.g., with the audio) to sexually stimulate the user associated with the sexual stimulation device. The one or more signals may be used to actuate the sexual stimulation device to perform one or more motion amplitudes of a predefined act.

In at least some exemplary embodiments, the exemplary disclosed system, apparatus, and method may include playing a piece of music on a mobile phone. The intensity of the vibration of the sexual stimulation device associated with the mobile phone may become stronger or weaker based on the rhythm of the music (e.g., on a regular basis with the rhythm of the music).

In at least some exemplary embodiments, the exemplary disclosed system may include an accessory control module, comprising computer-executable code stored in non-volatile memory, a processor, a device (e.g., user device 305 or model device 310) of a human user (e.g., user 320 or model 325), and an accessory (e.g., user accessory 308 or model accessory 315) configured to communicate with the device, the accessory including a motor or a heater. The accessory control module, the processor, the device, and the accessory may be configured to receive or obtain audio data using the device, identify at least one parameter of the audio data, the at least one parameter having one or more parameter values, convert the one or more parameter values into one or more action signals, and control the motor or the heater using the one or more action signals to perform a predefined act of the accessory at a parameter-dependent intensity synchronously with receiving or obtaining the audio data. The predefined act may sexually stimulate the human user. The at least one parameter may be at least one selected from the group of amplitude, period, frequency, pitch, timbre, volume, speed, decibels, and combinations thereof. The predefined act of the accessory that sexually stimulates the human user may be at least one selected from the group of vibration, rotation, swinging, inhalation, temperature variation, expansion, contraction, suction, and combinations thereof. The accessory control module, the processor, the device, and the accessory may be configured to change the parameter-dependent intensity of the predefined act proportionally to a change of the one or more parameter values synchronously with receiving or obtaining the audio data. When the audio data is a data stream of music, the parameter-dependent intensity of the predefined act may change proportionally to the one or more parameter values that correspond to the rhythm of the music synchronously with receiving or obtaining the data stream of the music. The accessory control module, the processor, the device, and the accessory may be configured to increase, synchronously with receiving or obtaining the audio data, the parameter-dependent intensity that may be a motion amplitude of the accessory as the one or more parameter values increases. The exemplary disclosed system may also include an application installed on the device, the application configured to send commands via Bluetooth or WiFi to the accessory to perform the predefined act via the one or more action signals. The audio data may be at least one selected from the group of music played in real-time, sound detected by the device in real-time, music or sound that is recorded but not played, and combinations thereof. Receiving or obtaining the audio data using the device may include playing streamed online music in real-time, playing music locally stored on the device in real-time, detecting and recording sound in real-time at a location of the device, and combinations thereof. When the audio data is music played in real-time or sound detected in real-time at a location of the device, converting the one or more parameter values into the one or more action signals may include decomposing a data file of the audio data in real-time to obtain the one or more parameter values, and controlling the motor or the heater may include actuating the accessory that may be a sexual stimulation device to perform the predefined act at the parameter-dependent intensity that may be a motion amplitude of the sexual stimulation device to sexually stimulate the human user. When the audio data may be music or sound that is recorded but not played, converting the one or more parameter values into the one or more action signals may include decomposing a data file of the audio data in real-time to obtain the one or more parameter values, and converting the one or more parameter values into action signals that may control the accessory at the parameter-dependent intensity that may be a motion amplitude of the accessory to sexually stimulate the human user. Converting the one or more parameter values into the one or more action signals may includes acquiring one or more designated frequency bands of the audio data, and generating the one or more action signals to drive the accessory to perform the predefined act based on the one or more designated frequency bands to sexually stimulate the human user with the accessory that may be a sexual stimulation device. Each of the one or more designated frequency bands may be a collection of frequencies within a certain range. Converting the one or more parameter values into the one or more action signals may include using a preset algorithm to determine the one or more action signals based on a preset sensitivity of one or more ranges. Controlling the motor or the heater may include actuating the accessory that may be a sexual stimulation device at the parameter-dependent intensity that may be a motion amplitude of the accessory based on the preset sensitivity of one or more ranges to sexually stimulate the human user.

In at least some exemplary embodiments, the exemplary disclosed method may include providing a device (e.g., user device 305 or model device 310) of a human user (e.g., user 320 or model 325), providing an accessory (e.g., user accessory 308 or model accessory 315) configured to communicate with the device, the accessory including a motor or a heater, receiving or obtaining audio data using the device, identifying at least one parameter of the audio data, the at least one parameter having one or more parameter values, converting the one or more parameter values into one or more action signals, and controlling the motor or the heater using the one or more action signals to perform a predefined act of the accessory at a parameter-dependent intensity synchronously with receiving or obtaining the audio data. The predefined act may sexually stimulate the human user. The at least one parameter may be at least one selected from the group of amplitude, period, frequency, pitch, timbre, volume, speed, decibels, and combinations thereof. The predefined act of the accessory that sexually stimulates the human user may be at least one selected from the group of vibration, rotation, swinging, inhalation, temperature variation, expansion, contraction, suction, and combinations thereof. The exemplary disclosed method may also include increasing, synchronously with receiving or obtaining the audio data, the parameter-dependent intensity that may be a motion amplitude of the accessory as the one or more parameter values increases. The exemplary disclosed method may further include providing a model device of a human model, providing a model accessory configured to communicate with the model device, the model accessory including a motor or a heater, and controlling the motor or the heater of both of the accessory and the model accessory using the one or more action signals to perform the predefined act at the parameter-dependent intensity synchronously with receiving or obtaining the audio data. The exemplary disclosed method may also include displaying video of the accessory sexually stimulating the human user and the model accessory sexually stimulating the human model in a chat room synchronously with receiving or obtaining the audio data.

In at least some exemplary embodiments, the exemplary disclosed system may include an accessory control module, comprising computer-executable code stored in non-volatile memory, a processor, a device (e.g., user device 305 or model device 310) of a human user (e.g., user 320 or model 325), and a sexual stimulation device (e.g., user accessory 308 or model accessory 315) configured to communicate with the device, the sexual stimulation device including a motor or a heater. The accessory control module, the processor, the device, and the sexual stimulation device may be configured to receive or obtain a data stream of sound or music using the device, identify at least one parameter of the data stream, the at least one parameter having one or more parameter values, convert the one or more parameter values into one or more action signals, control the motor or the heater using the one or more action signals to perform a predefined act of the sexual stimulation device at a parameter-dependent intensity synchronously with receiving or obtaining the data stream, and change the parameter-dependent intensity of the predefined act proportionally to a change of the one or more parameter values synchronously with receiving or obtaining the data stream. The predefined act sexually may stimulate the human user. The at least one parameter may be at least one selected from the group of amplitude, period, frequency, pitch, timbre, volume, speed, decibels, and combinations thereof. The predefined act of the sexual stimulation device that sexually stimulates the human user may be at least one selected from the group of vibration, rotation, swinging, inhalation, temperature variation, expansion, contraction, suction, and combinations thereof.

The exemplary disclosed system, apparatus, and method may provide an efficient and effective technique for controlling devices such as adult toys based on an operation of a user device such as a phone or a tablet of the user to sexually stimulate the user. The exemplary disclosed system, apparatus, and method may provide an efficient and effective technique for controlling devices such as adult toys based on ambient conditions surrounding users of adult toys. For example, the exemplary disclosed system, apparatus, and method may provide for control of devices such as adult toys based on music or sound played by a user device of the user or ambient sounds surrounding the user.

In at least some exemplary embodiments, the exemplary disclosed system, apparatus, and method may utilize sophisticated machine learning and/or artificial intelligence techniques to prepare and submit datasets and variables to cloud computing clusters and/or other analytical tools (e.g., predictive analytical tools) which may analyze such data using artificial intelligence neural networks. The exemplary disclosed system may for example include cloud computing clusters performing predictive analysis. For example, the exemplary neural network may include a plurality of input nodes that may be interconnected and/or networked with a plurality of additional and/or other processing nodes to determine a predicted result. Exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. The exemplary disclosed system may utilize prediction algorithms and approach that may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets.

Figure 11:
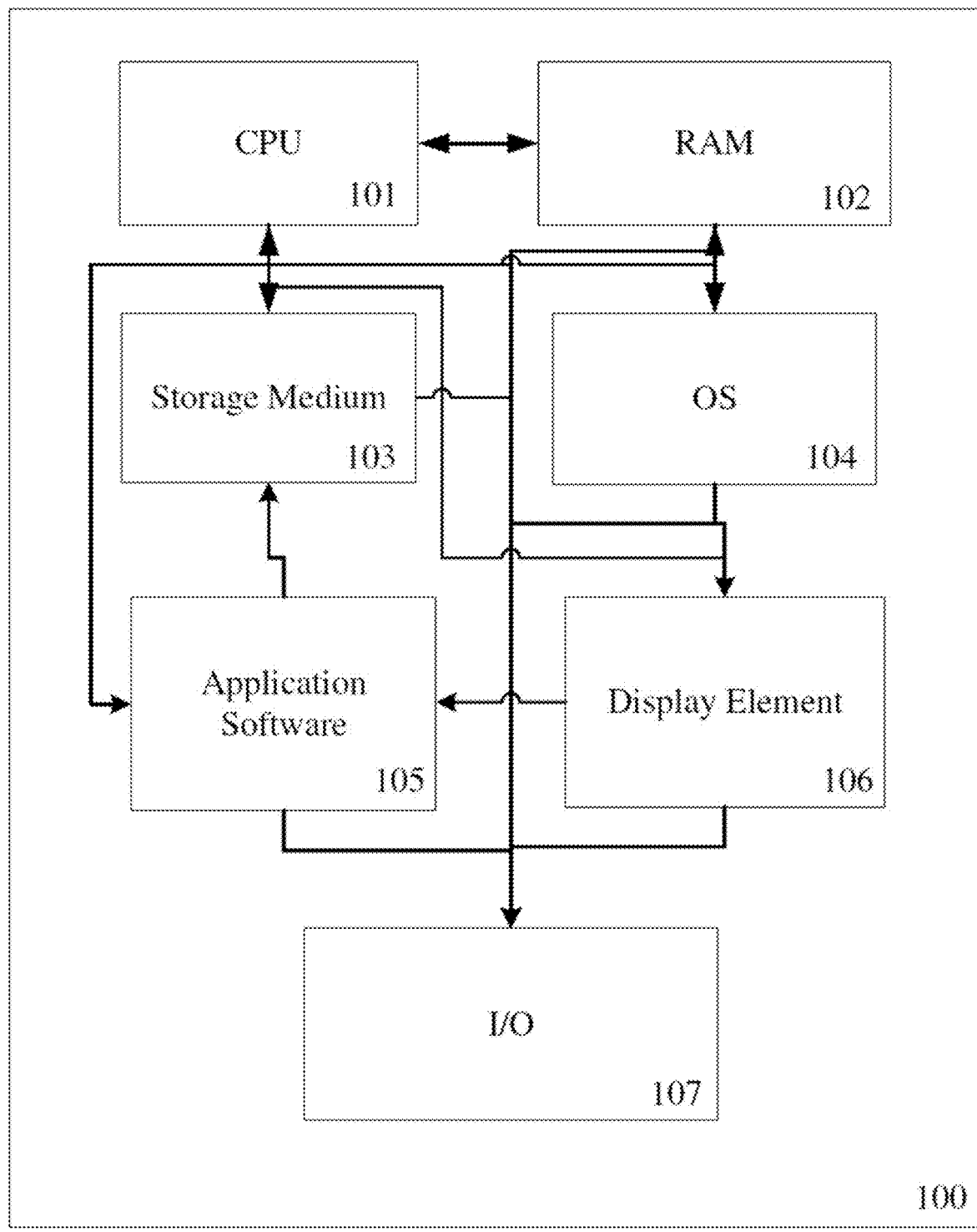
FIG. 11 is a schematic illustration of an exemplary computing device, in accordance with at least some exemplary embodiments of the present disclosure.

An illustrative representation of a computing device appropriate for use with embodiments of the system of the present disclosure is shown in FIG. 11. The computing device 100 can generally be comprised of a Central Processing Unit (CPU, 101), optional further processing units including a graphics processing unit (GPU), a Random Access Memory (RAM, 102), a mother board 103, or alternatively/additionally a storage medium (e.g., hard disk drive, solid state drive, flash memory, cloud storage), an operating system (OS, 104), one or more application software 105, a display element 106, and one or more input/output devices/means 107, including one or more communication interfaces (e.g., RS232, Ethernet, WiFi, Bluetooth, USB). Useful examples include, but are not limited to, personal computers, smart phones, laptops, mobile computing devices, tablet PCs, touch boards, and servers. Multiple computing devices can be operably linked to form a computer network in a manner as to distribute and share one or more resources, such as clustered computing devices and server banks/farms.

Various examples of such general-purpose multi-unit computer networks suitable for embodiments of the disclosure, their typical configuration and many standardized communication links are well known to one skilled in the art, as explained in more detail and illustrated by FIG. 12, which is discussed herein-below.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Figure 12:
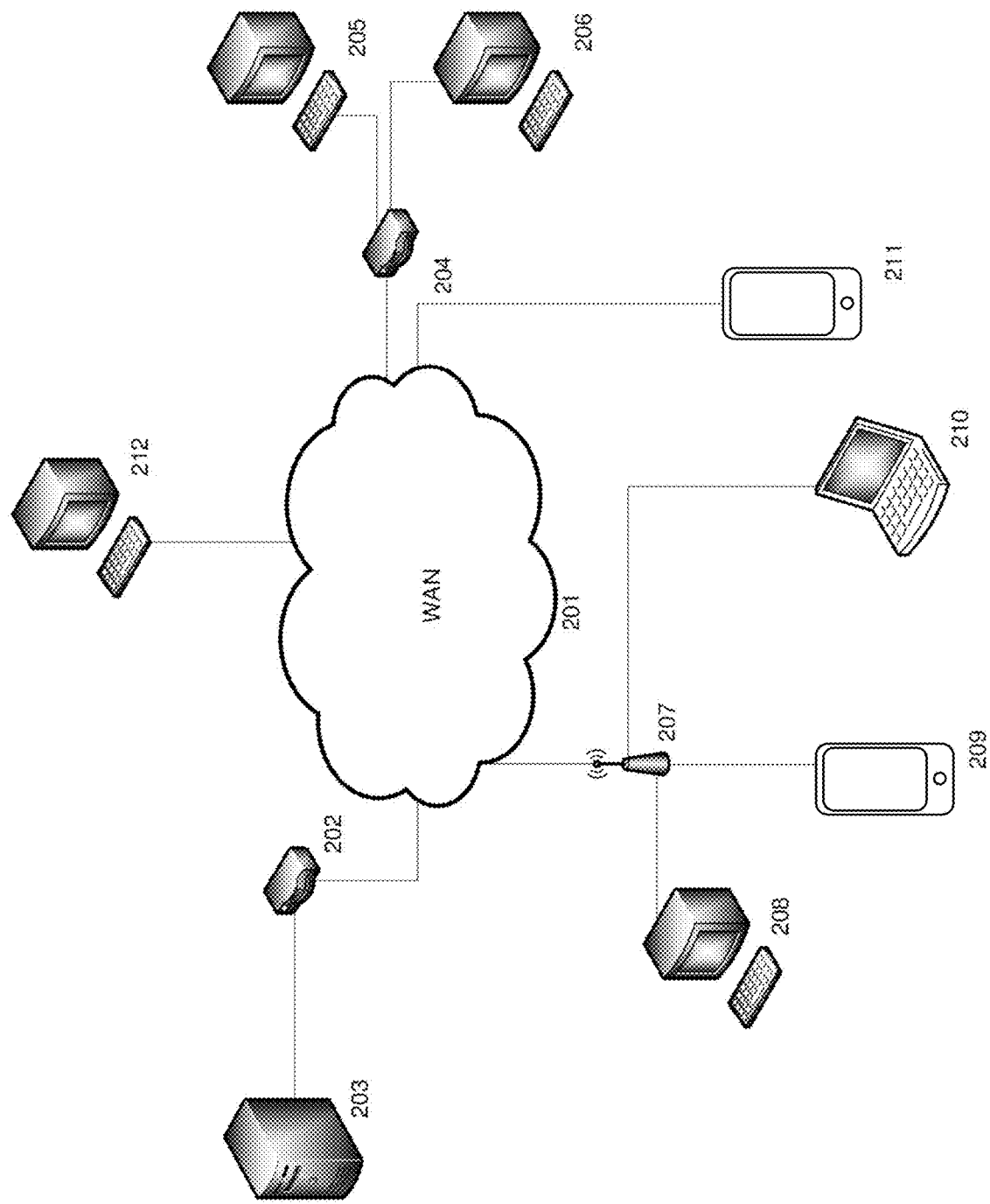
FIG. 12 is a schematic illustration of an exemplary network, in accordance with at least some exemplary embodiments of the present disclosure.

Referring to FIG. 12, a schematic overview of a system in accordance with an embodiment of the present disclosure is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 12, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present disclosure may or may not utilize one or more routers 202. One of ordinary skill in the art would appreciate that there are numerous ways server 203 may connect to WAN 201 for the exchange of information, and embodiments of the present disclosure are contemplated for use with any method for connecting to networks for the purpose of exchanging information. Further, while this application refers to high speed connections, embodiments of the present disclosure may be utilized with connections of any speed.

Components or modules of the system may connect to server 203 via WAN 201 or other network in numerous ways. For instance, a component or module may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GMS, 3G, 4G) to the WAN 201. One of ordinary skill in the art will appreciate that there are numerous ways that a component or module may connect to server 203 via WAN 201 or other network, and embodiments of the present disclosure are contemplated for use with any method for connecting to server 203 via WAN 201 or other network. Furthermore, server 203 could be comprised of a personal computing device, such as a smartphone, acting as a host for other computing devices to connect to.

The communications means of the system may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more threads. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A system, comprising:
   an accessory control module, comprising computer-executable code stored in non-volatile memory; and
   a processor;
   wherein the computer-executable code, when operating on the processor, causes the system to:
   activate an application installed in a device of a human user;
   establish communication between the device of the human user and an accessory based on the application, the accessory including a motor or a heater, wherein the device and the accessory are separate units;
   receive or obtain audio data using an audio sensor or an audio processing unit of the device;
   identify at least one parameter of the audio data, the at least one parameter having one or more parameter values including:
      decomposing a data file of the audio data in real-time to obtain the one or more parameter values; and
      converting the one or more parameter values into one or more action signals that control the accessory at a parameter-dependent intensity that is a motion amplitude of the accessory to sexually stimulate the human user;
   convert the one or more parameter values into the one or more action signals, including converting the one or more parameter values proportionally or inversely proportionally into said one or more action signals having intensity values for controlling the motor or the heater;
   play the audio data through a media player to obtain a sessionID, and obtain a corresponding visualizer through the sessionID to obtain an audio spectrum, the visualizer being of a display of the device that has the audio sensor or the audio processing unit; and
   control, based on sending the one or more action signals from the device to the accessory, the motor or the heater using the one or more action signals to perform a predefined act of the accessory at the parameter-dependent intensity;
   wherein the predefined act sexually stimulates the human user.

2. The system of claim 1, wherein the at least one parameter of the audio data is at least one selected from the group of amplitude, period, frequency, pitch, timbre, volume, speed, decibels, and combinations thereof.

3. The system of claim 1, wherein the predefined act of the accessory that sexually stimulates the human user is at least one selected from the group of vibration, rotation, swinging, inhalation, temperature variation, expansion, contraction, suction, and combinations thereof.

4. The system of claim 1, wherein the accessory control module, the processor, the device, and the accessory are configured to change the parameter-dependent intensity of the predefined act proportionally or inversely proportionally to a change of the one or more parameter values synchronously with receiving or obtaining the audio data.

5. The system of claim 4, wherein when the audio data is a data stream of music, the parameter-dependent intensity of the predefined act changes proportionally or inversely proportionally to the one or more parameter values that correspond to a rhythm of the music synchronously with receiving or obtaining the data stream of the music.

6. The system of claim 1, wherein the accessory control module, the processor, the device, and the accessory are configured to increase, synchronously with receiving or obtaining the audio data, the parameter-dependent intensity that is the motion amplitude of the accessory as the one or more parameter values increases.

7. The system of claim 1, wherein:
the audio data is at least one selected from the group of music played in real-time, sound detected by the device in real-time, music or sound that is recorded but not played, and combinations thereof; and
receiving or obtaining the audio data using the device includes at least one of playing streamed online music in real-time, playing music locally stored on the device in real-time, or detecting and recording sound in real-time at a location of the device.

8. The system of claim 1, wherein, when the audio data is music played in real-time or sound detected in real-time at a location of the device,
controlling the motor or the heater includes actuating the accessory that is a sexual stimulation device to perform the predefined act at the parameter-dependent intensity to sexually stimulate the human user.

9. The system of claim 1, wherein the audio data is music or sound that is recorded but not played.

10. The system of claim 1, wherein converting the one or more parameter values into the one or more action signals includes:
acquiring one or more designated frequency bands of the audio data; and
generating the one or more action signals to drive the accessory to perform the predefined act based on the one or more designated frequency bands to sexually stimulate the human user with the accessory that is a sexual stimulation device;
wherein each of the one or more designated frequency bands is a collection of frequencies within a certain range.

11. The system of claim 1, wherein:
converting the one or more parameter values into the one or more action signals includes using a preset algorithm to determine the one or more action signals based on a preset sensitivity of one or more ranges; and
controlling the motor or the heater includes actuating the accessory that is a sexual stimulation device at the parameter-dependent intensity based on the preset sensitivity of one or more ranges to sexually stimulate the human user.

12. The system of claim 1, wherein the accessory control module, the processor, the device, and the accessory are configured to:
associate a tipping signal of the human user with an activation command of an audio control function in advance; and
when receiving the tipping signal of the human user, activate the activation command to provide the audio control function to the human user;
wherein the tipping signal provides a sound that is perceived as rewarding or encouraging to the human user.

13. The system of claim 1, wherein identifying the at least one parameter of the audio data includes:
converting the audio data into digital signals; and
identifying at least one parameter of the digital signals, the at least one parameter of the digital signals having one or more parameter values.

14. The system of claim 1, wherein a change of the parameter-dependent intensity of the predefined act is progressive between levels, including moving through a plurality of levels.

15. A non-transitory computer-readable storage medium comprising computer-executable instructions that, when executed by at least one processor of a device of a human user, causes the device to perform a method, comprising:
activating an application installed in the device of the human user;
establishing communication between the device of the human user and an accessory based on the application, the accessory including a motor or a heater, wherein the device and the accessory are separate units;
receiving or obtaining audio data using an audio sensor or an audio processing unit of the device;
identifying at least one parameter of the audio data, the at least one parameter having one or more parameter values;
decomposing a data file of the audio data in real-time to obtain the one or more parameter values; and
converting the one or more parameter values into one or more action signals that control the accessory at a parameter-dependent intensity that is a motion amplitude of the accessory to sexually stimulate the human user;
converting the one or more parameter values into the one or more action signals, including converting the one or more parameter values proportionally or inversely proportionally into the one or more action signals having intensity values for controlling the motor or the heater;
play the audio data through a media player to obtain a sessionID, and obtain a corresponding visualizer through the sessionID to obtain an audio spectrum, the visualizer being of a display of the device that has the audio sensor or the audio processing unit; and
controlling, based on sending the one or more action signals from the device to the accessory, the motor or the heater using the one or more action signals to perform a predefined act of the accessory at the parameter-dependent intensity;
wherein the predefined act sexually stimulates the human user.

16. A method, comprising:
activating an application installed in a device of a human user;
establishing communication between the device of the human user and an accessory based on the application, the accessory including a motor or a heater, wherein the device and the accessory are separate units;
receiving or obtaining audio data using an audio sensor or an audio processing unit of the device;
identifying at least one parameter of the audio data, the at least one parameter having one or more parameter values including:
decomposing a data file of the audio data in real-time to obtain the one or more parameter values; and
converting the one or more parameter values into one or more action signals that control the accessory at a parameter-dependent intensity that is a motion amplitude of the accessory to sexually stimulate the human user;
converting the one or more parameter values into the one or more action signals, including converting the one or more parameter values proportionally or inversely proportionally into the one or more action signals having intensity values for controlling the motor or the heater;
play the audio data through a media player to obtain a sessionID, and obtain a corresponding visualizer through the sessionID to obtain an audio spectrum, the visualizer being of a display of the device that has the audio sensor or the audio processing unit; and controlling, based on sending the one or more action signals from the device to the accessory, the motor or the heater using the one or more action signals to perform a predefined act of the accessory at the parameter-dependent intensity;

wherein the predefined act sexually stimulates the human user.

17. The method of claim 16, wherein the at least one parameter of the audio data is at least one selected from the group of amplitude, period, frequency, pitch, timbre, volume, speed, decibels, and combinations thereof.

18. The method of claim 16, wherein the predefined act of the accessory that sexually stimulates the human user is at least one selected from the group of vibration, rotation, swinging, inhalation, temperature variation, expansion, contraction, suction, and combinations thereof.

19. The method of claim 16, further comprising increasing, synchronously with receiving or obtaining the audio data, the parameter-dependent intensity as the one or more parameter values increases.

20. The method of claim 16, further comprising:
providing a model device of a human model;
providing a model accessory configured to communicate with the model device, the model accessory including a motor or a heater; and
controlling the motor or the heater of both of the accessory and the model accessory using the one or more action signals to perform the predefined act at the parameter-dependent intensity synchronously with receiving or obtaining the audio data.

21. The method of claim 20, further comprising displaying video of the accessory sexually stimulating the human user and the model accessory sexually stimulating the human model in a chat room synchronously with receiving or obtaining the audio data.

22. The method of claim 16, further comprising:
associating a tipping signal of the human user with an activation command of an audio control function in advance; and
when receiving the tipping signal of the human user, activating the activation command to provide the audio control function to the human user.

* * * * *